United States Patent [19]

Timoney

[11] Patent Number: 5,183,659
[45] Date of Patent: Feb. 2, 1993

[54] PROTECTION OF EQUINES AGAINST STREPTOCOCCUS EQUI

[75] Inventor: John F. Timoney, Lansing, N.Y.

[73] Assignee: Cornell Research Foundation, Inc., Ithaca, N.Y.

[21] Appl. No.: 207,320

[22] Filed: Jun. 15, 1988

Related U.S. Application Data

[63] Continuation of Ser. No. 754,613, Jul. 12, 1985, abandoned.

[51] Int. Cl.$^5$ .................. A61K 39/02; C12N 15/00
[52] U.S. Cl. ........................... 424/92; 424/88; 435/172.1; 435/253.4; 435/885
[58] Field of Search ............. 435/172.1, 253.4, 885; 424/88, 92, 93

[56] References Cited

U.S. PATENT DOCUMENTS

| | | | |
|---|---|---|---|
| 3,793,150 | 2/1974 | Usdin | 424/92 |
| 3,852,420 | 12/1974 | Usdin | 424/92 |
| 4,169,886 | 10/1979 | Hertman et al. | 424/92 |
| 4,582,798 | 4/1986 | Brown et al. | 435/68 |
| 4,801,539 | 1/1989 | Akasaka et al. | 435/885 |

OTHER PUBLICATIONS

Bazeley, *Aust. Vet. J.* vol. 19, pp. 62-85, 1943.
Timoney et al., Abstract No.-172 appearing Abstracts IX, *Lancefield International Symposium on Streptococci and Streptococcal Disease*, Fugi, Japan, Sep. 10, 1984.
Galau et al, *Infection and Imumunity*, vol. 47, No. 3, pp. 623-628, Mar. 1985.
Timoney et al., *Infection and Immunity*, vol. 48, No. 1, pp. 29-34, Apr. 1985.

*Primary Examiner*—Johnnie R. Brown
*Assistant Examiner*—Abdel A. Mohamed
*Attorney, Agent, or Firm*—Ralph R. Barnard

[57] ABSTRACT

A new bacterial vaccine to protect susceptible equine against *S. equi* which causes strangles. The vaccine stimulates a nasopharyngeal immune response in a susceptible equine through the presence of antibody activity in the nasopharyngeal mucus. The vaccine is a *S. equi* strain which contains an M protein fragment of 41,000 mw and is adapted for administration to equine either intranasally or orally as a vaccine. There is described a new strain of *S. equi* (709-27), a method of making and isolating useful vaccine strain of *S. equi* bacteria which stimulates an antibody response in the nasopharyngeal mucosa of the susceptible equine.

10 Claims, 4 Drawing Sheets

IgG    IgA

PROTECTION OF EQUINES AGAINST STREPTOCOCCUS EQUI

This is a continuation of application Ser. No. 06/754,613, filed Jul. 12, 1985, now abandoned.

BACKGROUND OF THE INVENTION

This invention relates to the immunization of equines against *Streptococcus equi*. *S. equi* causes strangles, an acute upper respiratory tract disease of horses, characterized by fever, nasal discharge and abscess formation in the retropharyngeal and mandibular lymph nodes. Horses that have been so infected in the field or experimentally infected with strangles and which do recover from strangles become highly resistant to reinfection. Moreover, only one antigenic type of *S. equi* has been observed in the field.

The above notwithstanding, vaccines prepared from bacterins of *S. equi*, or fractional extracts of the same, such as M protein-rich extracts, have been relatively ineffective to provide protection against *S. equi* in the field. This is true even though as far back as 1943 an article entitled "Studies with Equine Streptococcus" published in the Australian Veterinary Journal at 19: 62 by P. O. Bazeley, presented a broad-range study of the problem coupled with test results which Dr. Bazeley and other characterized as very hopeful. However, many years have passed without an adequate or effective method or means for protection of equines against strangles. One of the problems with earlier experimentation in the field was that scientists and researchers equated protection of the horse against *S. equi* with stimulation of bactericidal antibodies in the blood serum of the horse. In fact, vaccine failure was not due to failure of vaccines to stimulate bactericidal antibody in the serum, which it was shown did not equate with protection against field or experimental exposure to *S. equi*. In fact, it was discovered that ponies recently recovered from experimentally induced strangles were highly resistant to reinfection before serum bactericidal activity could be detected. Moreover, it was determined that the nasopharyngeal mucus of resistant ponies contained major IgG and IgA antibody activity against only one acid extract protein of about 41,000 molecular weight (mw), whereas serum antibodies had a number of major specificities. These findings suggested that successful vaccination requires stimulation of the nasopharyngeal immune response.

The following publications have been made by the inventor herein relating to this development:

1) Abstract No. 172 appearing Abstracts IXth, *Lancefield International Symposium on Streptococci and Streptococcal Diseases*, Fuji, Japan, Sep. 10, 1984;
2) *Infection and Immunity*, March 1985, Vol. 47, No. 3, pages 623-628;
3) *Infection and Immunity*, April 1985, Vol. 48, No. 1, pages 29-34.

Tracks

Figure 1:
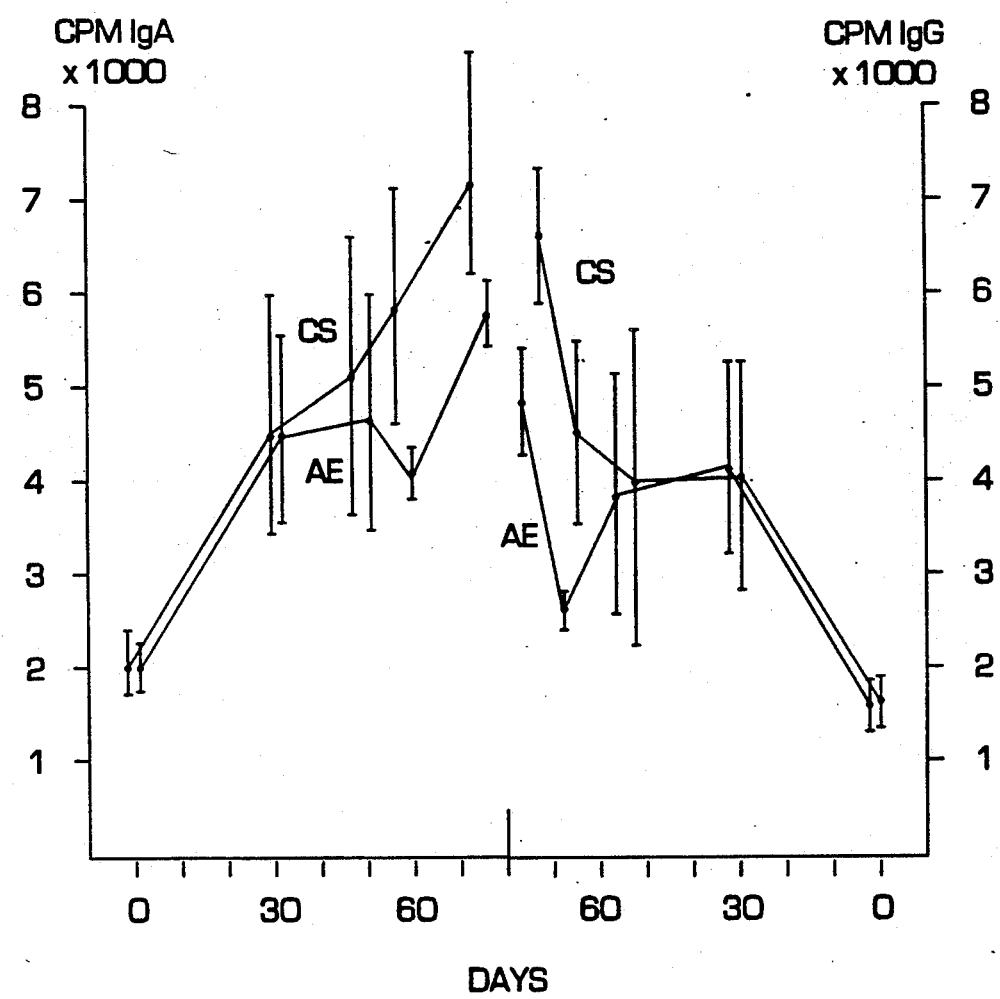
FIG. 1 is a graph with separate coordinates for the IgA and IgG antibody titers in nasal washes of 14 ponies against days which have passed following immunization with *S. equi* 709-27. The antigens in the radioimmunoassay were acid extract and culture supernatant (the native form) protein of *S. equi*.
Figure 2:
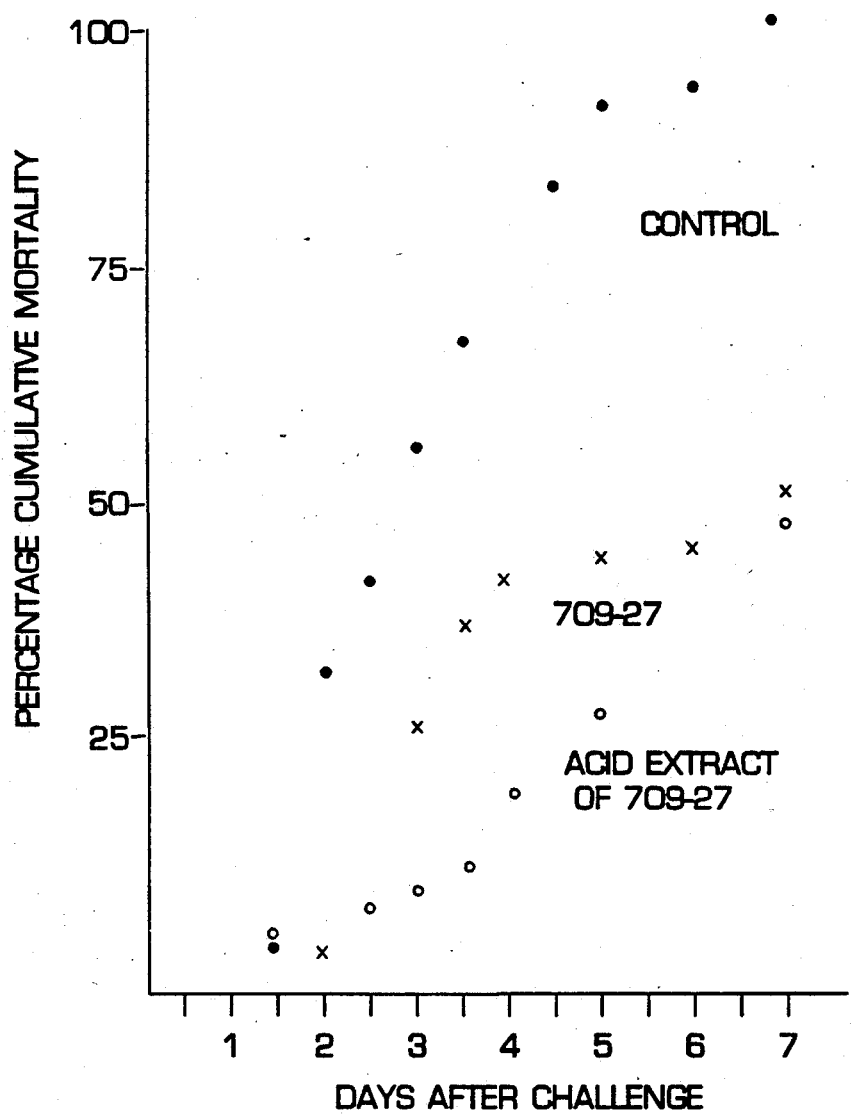
FIG. 2 is a graph of cumulative mortality against days after challenge for groups of 40 mice vaccinated with live *S. equi* 709-27, or an acid extract of *S. equi* 709-27 and a group of control non-immunized mice. All mice were challenged with $5 \times 10^{-7}$-CFU virulent *S. equi*. CF32. The information of FIG. 2 is important because it shows that *S. equi* 709-27 carries the intact M protein, similar to that of the parent *S. equi* CF32.
Figure 3B:
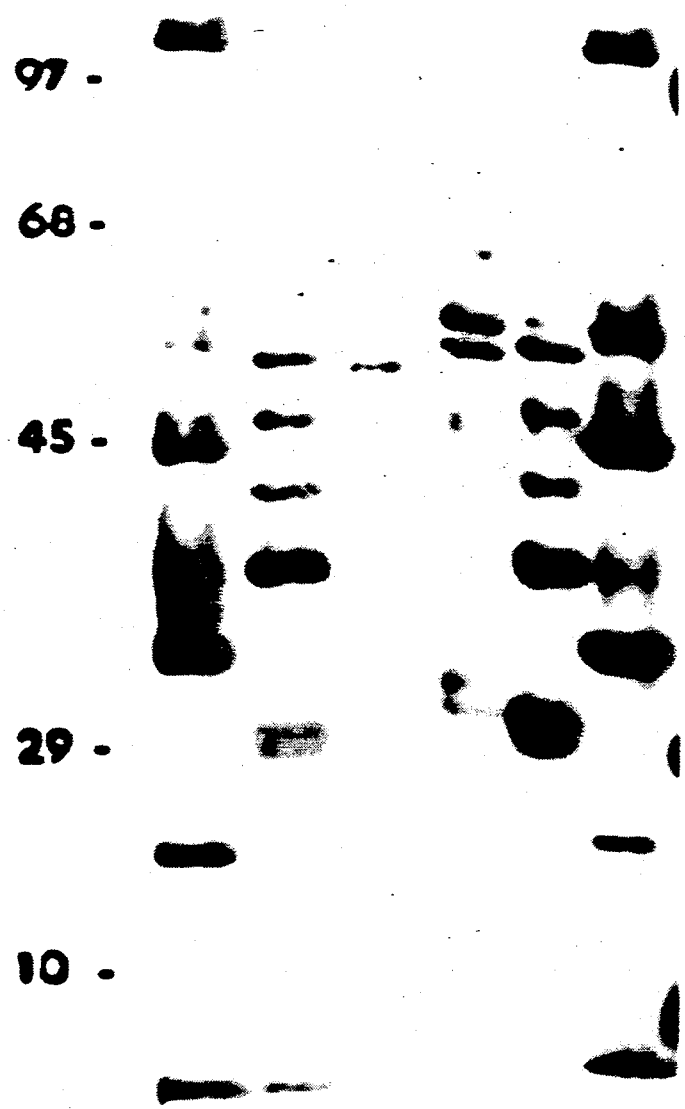
FIG. 3 is an immunoblot showing proteins (SDS PAGE), *S. equi* and *S. zooepidemicus* recognized by IgG and IgA in nasopharyngeal mucus and in serum of a pony following intranasal vaccination with *S. equi* 709-27. The blots were washed in monospecific antisera against equine IgA or IgG following treatment with nasopharyngeal mucus or serum.

A—Acid extract of *S. zooepidemicus*
B—Acid extract of *S. equi* (CF32)
C—Culture supernatant protein of *S. equi* (CF32)

Antigens of *S. zooepidemicus* were included because most horses carry this organism in the nasopharynx and therefore are stimulated to make antibodies to its proteins, some of which are common to *S. equi*.

The measurement technique described in the figures are similar to those discussed in the following publications:

a) *Infection and Immunity* Vol. 47, No. 3 pages 623-628 (March 1985);
b) *Infection and Immunity* Vol. 48, No. 1 pages 29-34 (April 1985).

DESCRIPTION OF THE INVENTION

The present invention teaches how to stimulate the nasopharyngeal immune response, for example using a bacterial clone derived from a highly virulent strain of *S. equi* known as *S. equi* CF32 which is on deposit at the American Type Culture Collection, (A.T.C.C. No. 53185) Rockville, Md., and available to the public as of the time this patent application is issued. CF32 produces large (1-3 mm) transparent, mucoid colonies that tend to flow together and are surrounded by a wide zone (5-10 mm) of beta hemolysis. Also on deposit with the American Type Culture Collection is a derivative of *S. equi* CF32 which has been rendered avirulent according to the teachings of the present invention. The avirulent derivative *S. equi* bacterium is known as Cornell *S. equi* 709-27 and will be available through the A.T.C.C. under A.T.C.C. No. 53186 when this patent application issues as a U.S. patent. Cornell 709–27 produces a small (0.5 mm in diameter white, convex smooth surfaced colony surrounded by a narrow (1 mm) zone of beta hemolysis.

This invention relates to an equine vaccine against *S. equi* caused strangles in an equine, which vaccine stimulates a nasopharyngeal immuno response in a strangles susceptible equine and which vaccine comprises an avirulent strain of *S. equi* formed by mutating a virulent strangles causing *S. equi* strain to render it avirulent while retaining thereon protein which provides an acid extract M protein fragment with a molecular weight of about 41,000 which stimulates an immunological response to IgG and IgA antibody similar to that in the nasopharyngeal mucus of an equine recovered from *S. equi* caused strangles.

The vaccine of the invention is not strain specific. Only one antigenic type of *S. equi* has been observed in the field. Thus, the method of the invention can be applied to any virulent strangles causing *S. equi* strain.

The virulent S. equi strain can be rendered avirulent in any manner so long as the resultant avirulent S. equi strain retains the M protein fragment having a molecular weight of about 41,000 which stimulates an immunological response similar to that in the nasopharyneal mucus of an equine recovered from S. equi caused strangles. The presently preferred method is deliberatedly induced mutagenesis for example by the use of chemicals or radiation. Particularly useful is chemical mutagenesis for example through the use of nitrosoguanidine. (See Chapter 13, Gene Mutation, *Manual of Methods of General Bacteriology*, American Society for Microbiology, Washington, D.C. 1981).

For the purposes of characterizing the vaccine of the invention through radio-immunoassay or immunoblotting assay the acid extract protein is isolated following techniques described in a publication by R. C. Lancefield entitled "The Antigenic Complex of Streptococcus Hemolyticus I Demonstration of a Type Specific Substance in Extracts of Streptococcus Hemolyticus" J. Exp. Med. 47:91.

For the purposes of further characterizing the vaccine of the invention protein molecular weight is determined by SDS-PAGE Electropheresis and the use of molecular weight standards.

In accordance with the teachings of the present invention a successful vaccine against S. equi requires stimulation of the nasopharyngeal immune response in a susceptible equine by intranasal or oral inoculation. Antibody activity in the nasopharyngeal mucus correlates with protection against strangles, and antibody activity in the blood serum is of less significance.

M-protein-rich extracts were relatively ineffective because they did not stimulate a nasopharyngeal immune response of the susceptible equine, although they were effective in producing an immune response in the blood serum of the animal. In order to stimulate the required response the present invention teaches a method of making avirulent S. equi bacteria which may be used as a vaccine and applied either intranasally or orally and produces major IgG and IgA antibody responses in the nasopharyngeal mucus of the susceptible equine. The avirulent strain of S. equi (Cornell 709-27) is such a bacteria. Hereinafter that especially made bacteria is called S. equi (Cornell 709-27).

Method of Producing an Effective Avirulent Vaccine Strain of S. equi

The strain of S. equi (Cornell 709-27) avirulent for mice and ponies was obtained in the following manner: the starting bacteria, S. equi CF32 was subjected to nitrosoguanidine mutagenesis following the teachings set out in an article by Carlton, B. C. and Brown, B. J. (1981) in Manual of Methods for General Bacteriology. (Eds. P. Gerhardt, et al) American Society for Microbiology, Washington, D. C., p. 226. Modification of the procedure setforth in the first column of page 226 was undertaken. Specifically, Todd Hewitt broth was used throughout the procedures as a growth medium. For example, reference is made to step 1 of the procedure in a verbatim copy of section 13.2.2 entitled "Nitrosoguanidine" on page 226 left-hand column of the above-identified publication copied hereinafter wherein Todd Hewitt broth was consistently substituted for the two alternative growth media therein identified.

13.2.2. Nitrosoguanidine

The methylating compound N-methyl-N'-nitro-N-nitrosoguanidine (NTG) is one of the most potent mutagens yet discovered for bacteria. It induces primarily base transitions, mutations of the GC→AT type, although AT→GC transitions, transversions, and even frameshifts arise at low frequencies.

Procedure.

1. Grow 10 ml of a suitable bacterial strain to the midlogarithmic stage (ca. $5 \times 10^8$ cells/ml) in L broth (13.9.1) or nutrient broth (13.9.11).

2. Centrifuge the culture for 5 min at $5,000 \times g$ to pellet the cells, and resuspend the cell pellet in an equal volume of Tris-maleic acid buffer (13.9.4) at pH 6.0.

3. Add a freshly prepared solution of NTG (1 mg/ml in sterile water) to the culture to a final concentration of 100 $\mu$g/ml. Incubate at 37° C. *without shaking* for 30 min.

4. Centrifuge the treated culture and resuspend the pellets in an equal volume of M56 minimal medium (13.9.8).

5. Recentrifuge the cells and again resuspend in M56 minimal medium (13.9.8). This procedure, devised by Adelberg et al. (5), yields a high degree of mutagenesis without the excessive cell killing which occurs when cells are treated in rich broth media (at least for *Escherichia coli*). It is particularly effective for the isolation of auxotrophic mutants (13.6.2).

Suggestions and possible problems.

CAUTION: NTG is not only a potent mutagen but also a carcinogen! Always employ all of the precautions outlined in part 13.2.

You may wish to determine a killing curve for NTG by plating $10^{-6}$ dilutions of both the untreated culture and the treated culture sampled at 5-min intervals during the NTG treatment (4). The conditions employed should produce no more that about 50% killing—higher concentrations will give more killing but may yield up to 40% auxotrophs among the survivors (5).

One of the potential difficulties in working with this mutagen is the likelihood of inducing multiple mutations in a small region of the bacterial chromosome (12). As a consequence, the mutants could have complex growth requirements due to mutations affecting more than one type of metabolic function and fail to revert to wild type at expected frequencies. It is thus wise to check NTG-induced mutants carefully for reversion before attempting to use them for further analysis (see 13.5.2)."

References in the above-quoted sections are to paragraphs the above-identified book entitled *Manual of Methods for General Bacteriology*. Nonencapsulated colonies were screened for loss of virulence by intraperitoneal inoculation of mice (ICR). The strains which did not kill mice were considered positive strains. The positive mouse strains were then used to vaccinate mice by the intraperitoneal route to determine their protective quality. Those strains which were protective of mice were inoculated intranasally into horses. Finally, as described herein, a derived strain of S. equi 709-27 was found to be avirulent in a dose of $3 \times 10^9$ CFU, and efficacious as a vaccine against S. equi in susceptible equine when it was intranasally or orally inoculated in the equine. Moreover, the positive strain which also protected equines tested for the presence of the 41 k fragment of the M protein by immunoblotting. The identifying number for that strain is S. equi 709-27.

An acid extract of strain S. equi (Cornell 709-27) was shown by immunoblotting to carry the same immunologically reactive proteins as the parent S. equi strain (CF32). The immunoblotting procedure used was similar to that used in a scientific article entitled "Infection and Immunity Vol. 48, No. 1 pages 29-34 (April 1985).

Equine Immunization and Challenge

The *S. equi* (Cornell 709-27) was then tested for efficacy as a vaccine against experimental *S. equi* infection in equine. The following table depicts that testing.

TABLE 1

Resistance of Ponies to Intranasal Challenge with Streptococcus equi Following Intranasal Immunisation with the Avirulent Strain of *S. equi* 709-27.

| Treatment (vaccinate with *S. equi* 709-27) | Challenge (CFU Virulent *S. equi* CF32) | No. Ponies | No. Resistant |
|---|---|---|---|
| $3 \times 10^9$ CFU Day 0 and Day 30 | $5 \times 10^8$ CFU Day 59 | 14 | 14 |
| Contact Controls | " | 2 | 2 |
| Isolation Controls | " | 6 | 0* |

*All controls developed acute strangles within 4 days of challenge.

Fourteen yearling ponies raised in isolation and never exposed to *S. equi* were given an atomized suspension (intranasally) of an 18 hour culture ($3\times10^9$ CFU) in Todd Hewitt broth of 709-27. A repeat inoculation was given 29 days later. Ponies were challenged intranasally 30 days later with $5\times10^8$ CFU of an overnight culture of *S. equi*. CF32. Cultures were administered by means of a nasal atomizer (Model #281, Devilbiss Co., Somerset, PA).

Six non-vaccinated ponies housed separately from the vaccinated group and 2 contact control ponies were also challenged with the same CF32 inoculum. All of the immunized ponies and the 2 contact control ponies were resistant to *S. equi* when challenged, but all of the isolation controls developed acute strangles whithin 4 days of challenge.

In addition about 800 horses on farms with endemic *S. equi* infection problems were experimentally intranasally or orally vaccinated with *S. equi* 709-27 to date and only two horses have developed strangles. The expected occurrence of strangles on those farms based on the experience of the three previous years, is such that one would have predicted the occurrence of strangles in the range of 40% of the horses.

When using the teachings of the present invention to vaccinate horses against *S. equi* the results of oral inoculation appeared to be comparable with intranasal inoculation with the same dose. The vaccine dose (number of organisms) used in the vaccination described herein was 100 times greater than the number of organisms of a wild virulent strain of *S. equi* (CF32), which would be expected to cause disease in a normal equine. However, a commercial *S. equi* vaccine program would ultilize dosage levels which were determined by consultation between the manufacturer and the appropriate governmental authorities.

Freezing or freeze drying does not adversely affect the vaccine. These procedures can therefore safely be used in mass production and distribution of the vaccine.

The vaccine has been entirely without side effect in adult animals, but a low ($\approx5\%$) incidence of submandibular abscesses has been observed on one occasion in 3-month foals. This adverse reaction occurred when a very heavy dose of vaccine was administered in an effort to obtain consistent seroconversion in the blood serum of the inoculated equine. As stated elsewhere, it is nasopharyngeal mucus of the susceptible equine that contains antibodies involved in immunological protection.

Antibody Assays — FIG. 1

IgA and IgG antibodies to the proteins of *S. equi* (CF32) were assayed in sera and nasal washes collected before, during, and after vaccination and challenge. Assays were performed by solid phase radioimmunoassay as described in an article entitled "Immunochemical Quantitation of Antigens by Single Radial Immunodiffusion" by G. Mancini, A. O. Carbonara and J. H. Heremans in *Immunochemistry* 2: pages 235-254. Wells were coated with acid extract (AE) or culture supernatant (CS) protein of *S. equi*.

IgA and IgG antibody responses to acid extract and culture supernatant proteins of *S. equi* were observed in nasal washes from all vaccinated animals (FIG. 1). Serum antibody responses were also observed, but they were inconsistent. Contact control ponies showed nasal and serum antibody conversion at the same time — an indication that transmission of the vaccine strain had occurred in the group. Principal and contact control ponies were resistant to challenge with virulent *S. equi* whereas non-vaccinated ponies developed typical strangles within 4 days of challenge (Table 1).

Mouse Immunization and Challenge — FIG. 2

The mouse has historically been the model for the immunology of *S. equi* infection. Accordingly, as a parallel test of efficacy, adult ICR mice were immunized subcutaneously with hydroxyapatite purified protein of an acid extract of *S. equi* 709-27. Reference is made to an article by Vosti, K. L. *Journal of Med. Microbiol.* 11:453 (1978). Protein was adsorbed to aluminum hydroxide and administered in two subcutaneous does of 50 ug 21 days apart. All mice, including a group of non-vaccinated controls, were later challenged with virulent *S. equi* ($5\times10^7$ CFU) given intraperitoneally. Mouse mortality was recorded for 7 days following challenge. The differences in mortality between the control and vaccinated groups was highly significant using the Chi square analysis used in statistics. The mice immunized either with an acid extract or live cells of *S. equi* 709-27 showed a significant protective response (probability $\leqq 0.01$) as compared with non-vaccinated controls (FIG. 2). This result suggests that *S. equi* 709-27 retained the protective M antigen of *S. equi*.

Notwithstanding the fact that it is not virulent, an acid extract of *S. equi* 709-27 was shown by immunoblotting to carry the same immunologically reactive proteins as the parent *S. equi* strain.

Figure 3A:
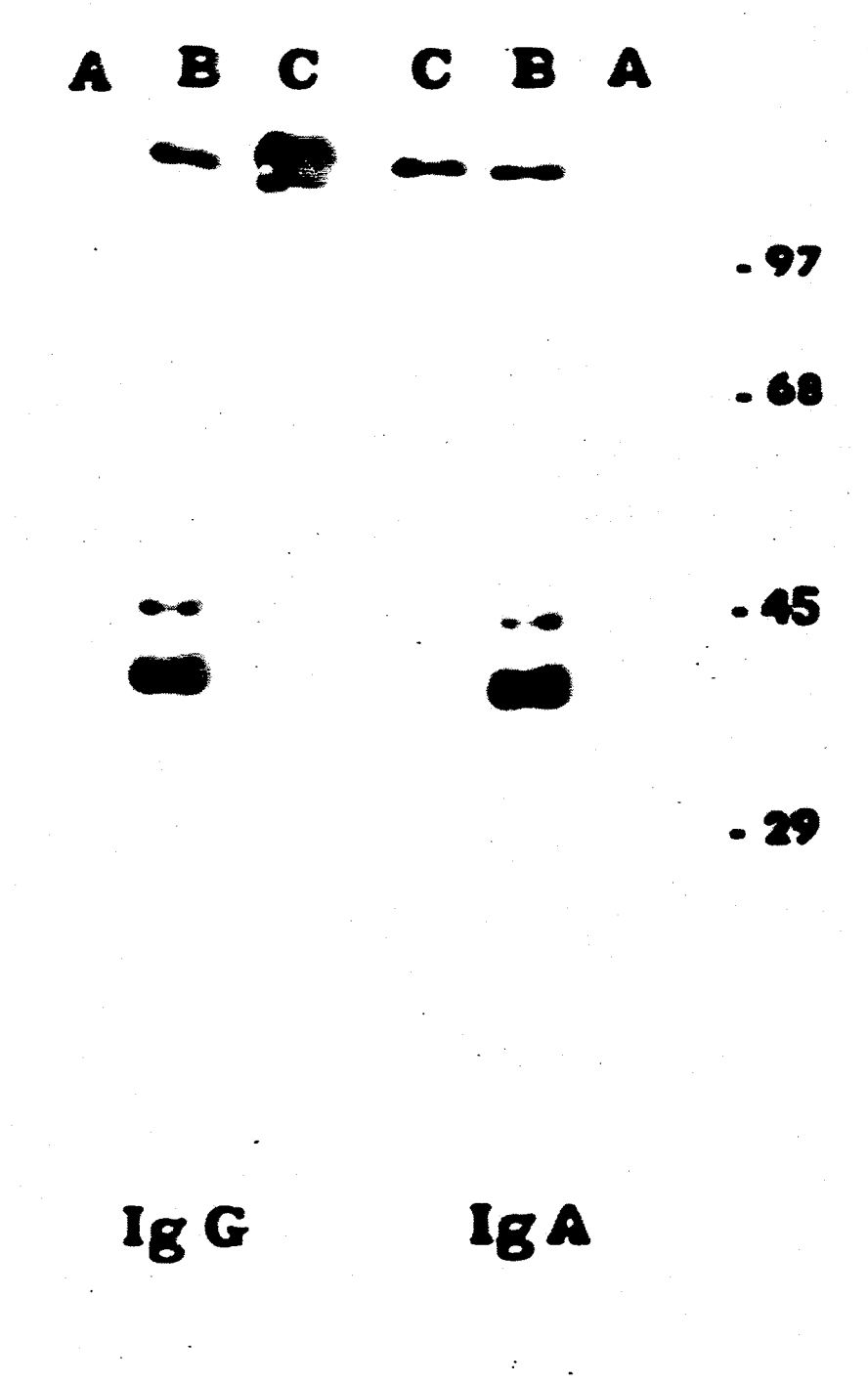

FIG. 3 Immunoblotting Showing Proteins Recognized by Mucosal and Serum Antibodies The immunologically reactive proteins in an acid extract and culture supernatant of *S. equi* and an acid extract of *S. zooepidemicus* were distinguished on nitrocellulose blots of SDS - PAGE gels. Blots were treated with sera or nasopharyngeal mucus collected when ponies were killed 7 days after challenge. A scientific article entitled "Infection and Immunity" Vol. 47, No. 3 pages 623-628 (March 1985) describes the technique used.

Immunoblotting revealed that IgA and IgG antibodies in nasopharyngeal mucus of vaccinated animals were directed mainly against a 41 k M protein fragment, whereas serum antibodies had a much broader spectrum of activity, a finding noted previously in ponies following recovery from experimentally induced strangles. Since an antibody response to the 41,000 mw M protein fragment is a constant feature of the nasopharyngeal immune response of resistant horses, it is an important protective antigen.

the antibody response is also specific to S. equi because similarly reactive proteins of S. zooepidemicus could not be detected on the immunoblot (Track A). Other studies have indicated that antibodies in strongly bactericidal sera react strongly with M protein fragments of about 29,000 and 37,000 molecular weight. A hypothesis to explain the different molecular weights of the M protein fragments of S. equi recognized by serum and nasopharyngeal antibody is that the portion or region of the M protein molecule of S. equi important in the nasopharyngeal response, differs from that involved in the stimulation of bactericidal antibody in serum.

In summary, the present invention teaches a new and improved bacterial vaccine to protect susceptible equine against S. equi which causes strangles. The vaccine stimulates a nasopharyngeal immune response in a susceptible equine through the presence of antibody activity in the nasopharyngeal mucus. The vaccine is a S. equi strain which contains an M-protein fragment of 41,000 mw and is adapted for administration to equine either intranasally or orally as a vaccine. The teachings of the present invention include: a new strain of S. equi (709-27), a method of making and isolating useful vaccine strain of S. equi bacteria, and which stimulates an antibody response in the nasopharyngeal mucosa of the susceptible equine.

Accordingly, it is to be understood that the embodiments of the invention herein described are merely illustrative of the application of the principles of the invention. Reference herein to details of the illustrated embodiments are not intended to limit the scope of the claims which themselves recite those features regarded as essential to the invention.

I claim:

1. A vaccine for protecting equines against S. equi which comprises an avirulent strain of S. equi known as S. equi 709-27 which can be inoculated intranasally or orally in the susceptible equine.

2. A vaccine for protecting equines against S. equi caused strangles which comprises an avirulent strain of S. equi 709-27 which stimulates an antibody response in the nasopharyngeal mucosa of the susceptible equine and includes an M-protein fragment with a molecular weight of about 41,000.

3. A method of protecting equines against virulent S. equi which comprises inoculating an equine either intranasally or orally with a strain of avirulent S. equi 709-27 which stimulates a nasopharyngeal antibody response in the nasopharyngeal mucosa of a susceptible equine.

4. The method of claim 3 wherein the strain of S. equi is both avirulent and carries at least M-protein fragments of about 41,000 mw.

5. A method of making a strain of S. equi which is avirulent for equines and usable as a vaccine for protecting equines against S. equi caused strangles comprising the following steps:
  1. subjecting a virulent strain of S. equi to mutagenesis;
  2. selecting a resulting nonencapsulated bacterium which provides an M-protein fragment having a molecular weight of about 41,000, which bacterium produces an S. equi antibody response in the nasopharyngeal mucosa of an S. equi susceptible equine.

6. A method of making a strain of S. equi which is avirulent for equines and usable as a vaccine for protecting equines against S. equi caused strangles comprising the following steps:
  1. subjecting a virulent strain of S. equi to mutagenesis through Nitrosoguanidine;
  2. selecting a resulting nonencapsulated bacterium which provides an M-protein fragment having a molecular weight of about 41,000, which bacterium stimulates an S. equi antibody response in the nasopharyngeal mucosa of an S. equi susceptible equine.

7. A vaccine against S. equi caused strangles in an equine, which vaccine stimulates a nasopharyngeal S. equi antibody response in a strangles susceptible equine comprising an avirulent strain of S. equi which stimulates an antibody response in the nasopharyngeal mucosa of the susceptible equine wherein said strain of avirulent S. equi is nonencapsulated and includes an M-protein fragment with a molecular weight of about 41,000 and the strain of avirulent S. equi is S. equi 709-27.

8. A vaccine against S. equi caused strangles in an equine, which vaccine stimulates a nasopharyngeal S. equi antibody response in a strangles susceptible equine comprising a strain of avirulent S. equi including an M-protein fragment with a molecular weight of about 41,000 and which can be inoculated intranasally or orally and wherein the strain avirulent S. equi is S. equi 709-27.

9. A vaccine for protecting equines against S. equi caused strangles which comprises an avirulent strain of S. equi which stimulates an antibody response in the nasopharyngeal mucosa of the susceptible equine which comprises an avirulent strain of S. equi formed by mutating using nitrosoguanidine a virulent strangles causing S. equi strain to render it avirulent and nonencapsulated while retaining thereon protein which provides an M-protein fragment with a molecular weight of about 41,000 which stimulates an immunological response in the form of IgG and IgA antibodies in the nasopharyngeal mucosa of an equine similar to that found in an equine which has recovered from S. equi caused strangles.

10. A method of protecting equines against virulent S. equi which comprises the inoculation of an equine either intranasally or orally with a strain of avirulent S. equi which is nonencapsulated and carries at least a M-protein fragment of about 41,000 mw and which is produced by the mutagenesis of a virulent strain of S. equi with Nitrosoguanidine.

* * * * *